(12) United States Patent
Eikelmann et al.

(10) Patent No.: US 9,486,569 B2
(45) Date of Patent: Nov. 8, 2016

(54) SPIKE WITH NON-RETURN VALVE FUNCTION AND FILLING DEVICE OF A LIQUID SYSTEM WITH SPIKE

(71) Applicant: B. BRAUN AVITUM AG, Melsungen (DE)

(72) Inventors: Guido Eikelmann, Baunatal (DE); Rainer Hector, Osnabrueck (DE)

(73) Assignee: B. BRAUN AVITUM AG, Melsungen (DE)

( * ) Notice: Subject to any disclaimer, the term of this patent is extended or adjusted under 35 U.S.C. 154(b) by 0 days.

(21) Appl. No.: 14/784,134

(22) PCT Filed: Apr. 16, 2014

(86) PCT No.: PCT/EP2014/057745
§ 371 (c)(1),
(2) Date: Oct. 13, 2015

(87) PCT Pub. No.: WO2014/170379
PCT Pub. Date: Oct. 23, 2014

(65) Prior Publication Data
US 2016/0030656 A1 Feb. 4, 2016

(30) Foreign Application Priority Data

Apr. 19, 2013 (DE) .................. 10 2013 103 986

(51) Int. Cl.
*A61M 37/00* (2006.01)
*A61M 1/36* (2006.01)
(Continued)

(52) U.S. Cl.
CPC .......... *A61M 1/3647* (2014.02); *A61M 1/367* (2013.01); *A61M 1/3643* (2013.01); *A61M 39/223* (2013.01); *F16K 11/02* (2013.01);
(Continued)

(58) Field of Classification Search
CPC .......... A61M 1/3647; A61M 1/3643; A61M 1/367; A61M 39/223; F16K 11/02; F16K 11/072; F16K 15/18; F16K 31/60
USPC ................................ 604/4.01–6.11
See application file for complete search history.

(56) References Cited

U.S. PATENT DOCUMENTS 3,827,601 A 8/1974 Magrath
4,397,335 A 8/1983 Doblar
(Continued)

FOREIGN PATENT DOCUMENTS

CA 2807013 2/2012
CN 1809393 7/2006
(Continued)

OTHER PUBLICATIONS

German Search Report for German Application No. 10 2013 103 986.3 mailed Oct. 16, 2013, including partial translation.
(Continued)

*Primary Examiner* — Philip R Wiest
(74) *Attorney, Agent, or Firm* — RatnerPrestia

(57) ABSTRACT

Disclosed is an anti-contamination device for preventing contamination of a fluid stored in a fluid container with a spike and a manually operable fluid blocking mechanism arranged directly downstream of the spike. A non-return valve is arranged between the spike and the fluid blocking mechanism, and that valve is adapted to allow only a flow from the spike in the direction of the manually operable fluid blocking mechanism.

15 Claims, 4 Drawing Sheets

(51) Int. Cl.
- *A61M 39/22* (2006.01)
- *F16K 11/02* (2006.01)
- *F16K 15/18* (2006.01)
- *F16K 31/60* (2006.01)
- *F16K 11/072* (2006.01)

(52) U.S. Cl.
CPC .......... *F16K 11/072* (2013.01); *F16K 15/18* (2013.01); *F16K 31/60* (2013.01)

(56) References Cited

U.S. PATENT DOCUMENTS

| | | |
|---|---|---|
| 4,819,653 A | 4/1989 | Marks |
| 4,844,810 A | 7/1989 | Richalley |
| 5,259,961 A | 11/1993 | Eigendorf |
| 5,334,315 A | 8/1994 | Matkovich |
| 5,540,653 A | 7/1996 | Schock |
| 5,669,879 A | 9/1997 | Duer |
| 8,343,098 B2 | 1/2013 | Nystrom et al. |
| 8,617,093 B2 | 12/2013 | Kopperschmidt et al. |
| 2003/0125673 A1 | 7/2003 | Houde |
| 2010/0191106 A1 | 7/2010 | Koyama |
| 2011/0137224 A1 | 6/2011 | Ibragimov |
| 2011/0208128 A1 | 8/2011 | Wu |
| 2013/0131609 A1 | 5/2013 | Kawashima |
| 2013/0139901 A1 | 6/2013 | Haecker et al. |

FOREIGN PATENT DOCUMENTS

| | | |
|---|---|---|
| CN | 102458503 | 5/2012 |
| CN | 102655890 | 9/2012 |
| CN | 103002933 | 3/2013 |
| CN | 103052416 | 4/2013 |
| DE | 4208274 | 10/1993 |
| EP | 2158934 | 3/2010 |
| WO | 8806895 | 9/1988 |

OTHER PUBLICATIONS

International Search Report for International Application No. PCT/EP2014/057744 mailed Aug. 8, 2014.
International Search Report for International Application No. PCT/EP2014/057745 mailed Aug. 7, 2014.
International Search Report for International Application No. PCT/EP2014/057749 mailed Jul. 31, 2014.
Chinese Office Action and Search Report for CN 201480022287.6, with translation, dated May 25, 2016.
Chinese Office Action and Search Report for CN 201480022273.4, with translation, dated Jun. 15, 2016.
Notice of Allowance for U.S. Appl. No. 14/783,266 dated Aug. 26, 2016.

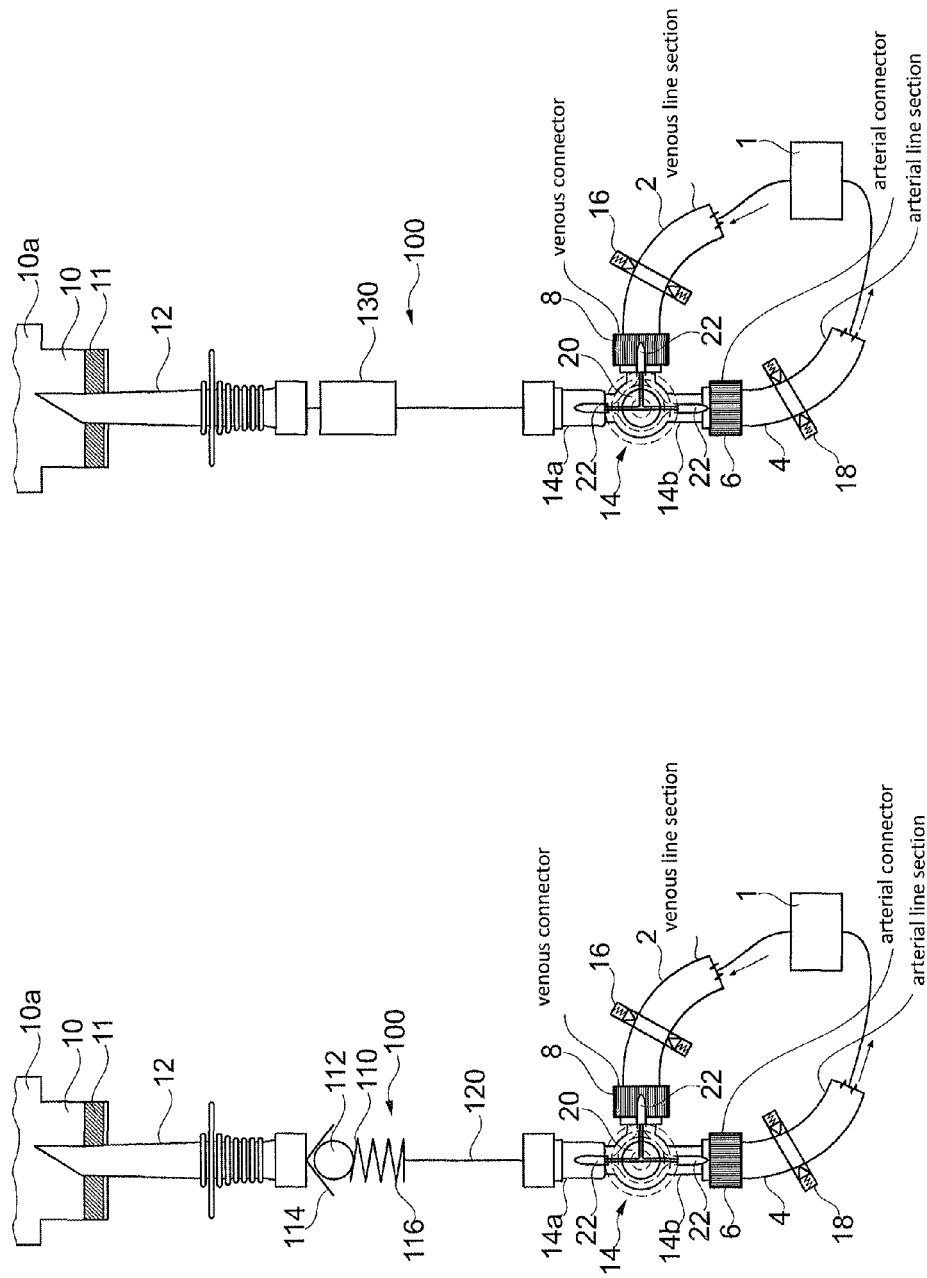

SPIKE WITH NON-RETURN VALVE FUNCTION AND FILLING DEVICE OF A LIQUID SYSTEM WITH SPIKE

CROSS REFERENCE TO RELATED APPLICATIONS

This application is the U.S. national phase application of PCT International Application No. PCT/EP2014/057745 filed Apr. 16, 2014, which claims priority to German Patent Application No. DE 10 2013 103 986.3 filed Apr. 19, 2013, the contents of each application being incorporated by reference herein.

FIELD OF THE INVENTION

The invention in hand concerns a spike with a non-return valve function check valve function and the filling device of a fluid conducting system and/or liquid system, in particular of an extracorporeal blood treatment device, for example a dialysis or apheresis machine, that is equipped with the spike with non-return valve function.

BACKGROUND OF THE INVENTION

In particular, the hydraulic system (blood side fluid system) of a blood treatment device, for example a dialysis machine, has to be filled with fluid, for example an NaCl solution or another sterile physiological solution, before being connected up to a patient, in such a way that air pockets in the system that would be dangerous for a patient connected up to the fluids of the system are eliminated. Furthermore, the hydraulic system should optionally be flushed with the filled-in fluid for a certain period of time in order to filter/wash out any contaminants, dirt particles, etc. that may have deposited in the system before the system is connected up to the patient. On an extracorporeal blood treatment device, these two procedures are performed in the scope of a filling cycle and optionally a circulation cycle.

In the state of the art, there are fluid containers preferably in the shape of plastic bags designed especially for extracorporeal blood treatment devices of this relevant type in order to enable, among others, the device functions as defined above. This kind of fluid container is also manufactured and sold by the applicant filing the application in hand.

As a rule, such a fluid container has a fluid intake chamber and two preferably closable fluid connectors. On a first of the two connectors, an arterial line section, and on the second connector, a venous line section of the hydraulic system (fluid system or also referred to as fluid conducting system) of the extracorporeal blood treatment device can be connected. The fluid bag as well as the two line sections together constitute a circulation device of the extracorporeal blood treatment device.

For the fluid system filling process, first the arterial line section is connected to the first fluid connector of the bag, and after opening of the first fluid connector, the hydraulic system is filled. The venous line section of the system first remains open to the atmosphere or is connected to a drain, a container or a bag so that air inside the system can escape and be vented in the atmosphere. As soon as the filling process is completed, the venous line section is connected to the second fluid connector of the bag in order to circulate the fluid inside the hydraulic system of the extracorporeal blood treatment device for a certain period of time or a certain volume of flow through the bag chamber.

During this circulation process, the fluid flows through internal filtering devices in which remaining air pockets are removed/filtered out with the fluid. If necessary, the venous line section of the hydraulic system can again be disconnected from the second fluid connector of the fluid bag and the fluid inside the hydraulic system can be flushed out again under constant supply of fluid from the container.

Upon termination of the circulation process, the filling/circulation cycle preparing for patient treatment is completed so that the two line sections (venous and arterial) can be disconnected from the fluid bag and connected up to the patient for treatment.

The description above of the filling/circulation cycle of a hydraulic system/fluid conducting system of an extracorporeal blood treatment device (dialysis machine) known from the state of the art indicates that the fluid bag remains in the system circuit for the filling and circulation processes, i.e. that the fluid inside the system is circulated through the fluid bag and/or its fluid chamber. As a result, the fluid in the fluid bag may get contaminated. The consequence of this is that with each new treatment preparation of the extracorporeal blood treatment device, a new fluid bag with fresh, uncontaminated fluid is used for the following filling/circulation cycle, whereas the fluid bag for the filling/circulation cycle performed before is disposed of independently of its residual content. It is obvious that this procedure results in the wasting of a large quantity of fluid in case of a high patient treatment number because the fluid content of a fluid bag can only be used (incompletely) for one filling/circulation cycle.

Furthermore, the fluid bags for blood treatment devices effectively concern a custom-made design with two separate fluid connectors, as a result of which manufacturing becomes more expensive due to smaller numbers as compared with conventional NaCl bags/bottles on the whole.

SUMMARY OF THE INVENTION

Considering these problems, the purpose of the invention in hand is to make available a technical device in particular for a class-specific filling device of a fluid conducting system of this kind, preferably an extracorporeal blood treatment device, with which contamination of a fluid bag that is connected to it or can be connected to it can be prevented. Furthermore, it is a purpose of the invention in hand to make available a filling device and a filling procedure which can be operated more efficiently and so more cost-effectively as compared to the state of the art.

Furthermore, a purpose of the invention in hand is to make available a fluid system equipped with the filling device according to aspects of the invention, for example an extracorporeal blood treatment device, that can be operated in a simple manner and that enables the use of conventional fluid bottles (e.g. NaCl bottles).

This task is completed with an anti-contamination device (means for prohibiting contamination), a filling device of a fluid system/liquid system (means for filling a fluid liquid system), preferably an extracorporeal blood treatment device (dialysis, apheresis machine), a fluid conducting system (means for conducting fluid), and a procedure as set forth in the claims. Advantageous embodiments of the invention are the object of sub-claims.

The basic idea of the invention in hand is to design the class-specific filling device of a fluid conducting system, in particular an extracorporeal blood treatment system, in such a way and/or to equip it with such a device that a conventional (price-effective) fluid container of a known design such as a conventional NaCl bottle or a suitable bag with a single puncturable/connectable connector can be used.

Consequently according to aspects of the invention, a suitable anti-contamination device is provided with a spike (spike-like means) for connecting a fluid container (NaCl bottle/bag) and a manually operable fluid blocking mechanism for the optional fluid connecting of the fluid container with a fluid conducting system to be filled, which can be connected to the fluid blocking mechanism. Thus the fluid blocking mechanism (means for blocking fluid) is arranged directly downstream of the spike, whereby the fluid blocking mechanism can be coupled directly with the spike, or a connecting hose section can be interposed between the fluid blocking mechanism and the spike. In addition according to aspects of the invention, a non-return valve (means for allowing fluid flow only in one direction) is provided between spike and fluid blocking mechanism, which is adapted in such a way that it allows only one flow from the spike in the direction of the manually operable fluid blocking mechanism.

Furthermore, the filling device according to aspects of the invention has, as a central component, the so-called spike (means) for connecting up the single fluid connector of a conventional medical fluid container e.g. NaCl bottle (means for storing medical fluid), to which the manually operable fluid blocking mechanism, for example a stop valve, is connected downstream, which is adapted or provided in such a way so as to remain constantly fluidically connected with the spike. The fluid blocking mechanism has at least one fluid outlet connector, which is adapted so that a line section/hose of a fluid conducting system/fluid system, preferably the arterial line section of a blood purification device/dialysis machine, can be connected to it in a detachable manner. Here the non-return valve can be arranged in the spike outlet, in the connecting hose section or in the inlet of the manually operable fluid blocking mechanism to which the spike is connected.

As a result of the arrangement of the fluid blocking mechanism on the spike, the spike can remain on the conventional medical fluid container after puncturing of the container seal, whereas the arterial line section can optionally be connected to the fluid blocking mechanism for a filling process of the fluid conducting system and then be disconnected again from the fluid blocking mechanism without losing any fluid from the medical fluid container. As the arterial line section is uncoupled from the outlet connector of the fluid blocking mechanism (e.g. Luer-Lock fitting), the arterial line section can be reconnected to an arterial patient access immediately afterwards without any changes having to be performed on the arterial line section and/or its connector. This simplifies the handling of the filling device.

Furthermore, the non-return valve reliably prevents a reverse of flow in the fluid container independently of the activation position of the fluid blocking mechanism.

This means that even if the fluid blocking mechanism is activated unintentionally or erroneously or has a malfunction, the non-return valve acts as a "fail-safe" device.

Preferably, the fluid blocking mechanism is a 3-way switch, for example a Y- or T-piece, and more preferably a 3-way valve, whereby the conduits/connectors can optionally be shut off manually (for example with clamps on the conduits/connectors or with the valve) in order to close off the conduits completely and/or to fluidically connect the conduits optionally and/or to allow a fluid flow at least between two selected conduits. According to aspects of the invention, the 3-way switch, preferably the 3-way valve, is arranged directly downstream of this one, preferably universal medical fluid container. In the specific case, a first connector of the 3-way switch (of the 3-way valve) is coupled with the so-called spike (or a different connecting device) or is designed with it (integral with the spike), with which a fluid chamber of the fluid container can be tapped. To a second connector of the 3-way switch (of the 3-way valve), the arterial line section, and to a third connector of the 3-way switch (of the 3-way valve), a venous line section of the fluid system can be connected. The 3-way switch, preferably the 3-way valve, can furthermore preferably be put and/or switched manually in at least three positions from which in a first switch position, the first connector is exclusively fluidically connected with the second connector and/or a fluid flow between these two connectors is possible and the third connector is closed (flush position and/or supply switch position and/or single-pass switch position), in a second switch position, the second connector is fluidically connected with the third connector and/or a fluid flow between these two connectors is possible and the first connector is closed (circulation switch position), and in a third switch position, all three connectors are separated from each other and/or closed (therapy switch connector or closed switch connector).

A medical fluid/liquid system equipped in such a way enables the coupling of the conventional fluid container with the arterial line section for the filling process (with the venous line section disconnected) by putting the 3-way switch, preferably the 3-way valve, in the first switch position, and connecting the arterial line section with the venous line section for the circulation process by putting the 3-way switch, preferably the 3-way valve, in the second switch position. As the first connector of the 3-way switch, preferably the 3-way valve, is closed in this second switch position, the fluid container is disconnected from the hydraulic system/circuit of the extracorporeal blood treatment device so the remaining fluid in it is not contaminated by the fluid circulating in the hydraulic system. As in the third switch position of the 3-way switch, preferably the 3-way valve, all of its connectors are closed, the two line sections of the hydraulic system can be disconnected in this switch position and connected to the patient for treatment.

As a result, the fluid container can be used for several treatment steps or for several phases within a treatment depending on the fill volume so that no fluid is lost any more. Furthermore, the medical filling device is provided for a conventional/universal medical fluid container, which is more cost-efficient in comparison with the specially designed containers with two connectors for extracorporeal blood treatment devices. Finally, the fluid container used does not require any connector, in particular for the case that the so-called spike is connected to the 3-way switch, preferably the 3-way valve, or is combined with it into an integral modular unit. In the latter case, the spike can be connected effectively transition-free, i.e. without interposition of a (bridging) pipe section, directly with the first connector, preferably in one piece, or screwed on it.

The medical fluid system/fluid conducting system according to aspects of the invention, preferably a blood purification system (dialysis machine), has a filling device according to the design described above and a venous blood conduit section and an arterial blood conduit section, of which at least the arterial section is adapted in such a way that it is/can be optionally connected to the filling device.

Furthermore, at least the arterial line section has, directly downstream of its connector interacting with the filling device, (a component) a blocking mechanism (e.g. a hose clamp as further component) with which the arterial line section can be temporarily fluidically closed for reconnecting from the filling device to an arterial patient access and vice versa. Preferably the venous line section has the same components as the arterial line section.

BRIEF DESCRIPTION OF THE DRAWINGS

The invention is best understood from the following detailed description when read in connection with the accompanying drawings. Included in the drawings are the following figures:

FIGS. 6a, 6b, 6c and 6d show symbolically the anti-contamination device of the filling device on different positions between the spike and the manually operable blocking mechanism, preferably in the form of the 3-way valve.

DETAILED DESCRIPTION OF THE PREFERRED EMBODIMENTS

According to FIG. 1, an extracorporeal blood treatment device 1, for example a dialysis or apheresis machine, has an internal hydraulic conducting system (hereinafter referred to as fluid conducting system) through which during a treatment phase on the machine side, for example, a blood purification fluid (dialysis fluid) is passed, and on the patient side, blood flows through it extracorporeally, whereby the machine-side and the patient-side fluid conducting systems are fluidically separated in case of a dialysis machine by a dialyser (filter) that is not shown in more detail.

For this purpose, the fluid conducting system has a venous line section and an arterial line 2, 4 on the patient side, preferably with connectors (Luer-Lock fittings) 6, 8 on each hose section arranged/formed on the ends in each case to which, for example, injection needles or cannulas (not depicted) can be connected as patient access, which can be introduced in a patient's body.

In order to avoid a possibly necessary washing out of possible contaminations, resulting from manufacturing, in the patient's body, the extracorporeal blood treatment device 1 has a filling device which enables a circulation process (consequently hereinafter referred to a circulation device) with which the fluid conducting system is cleaned as a rule before every patient treatment.

Figure 1:
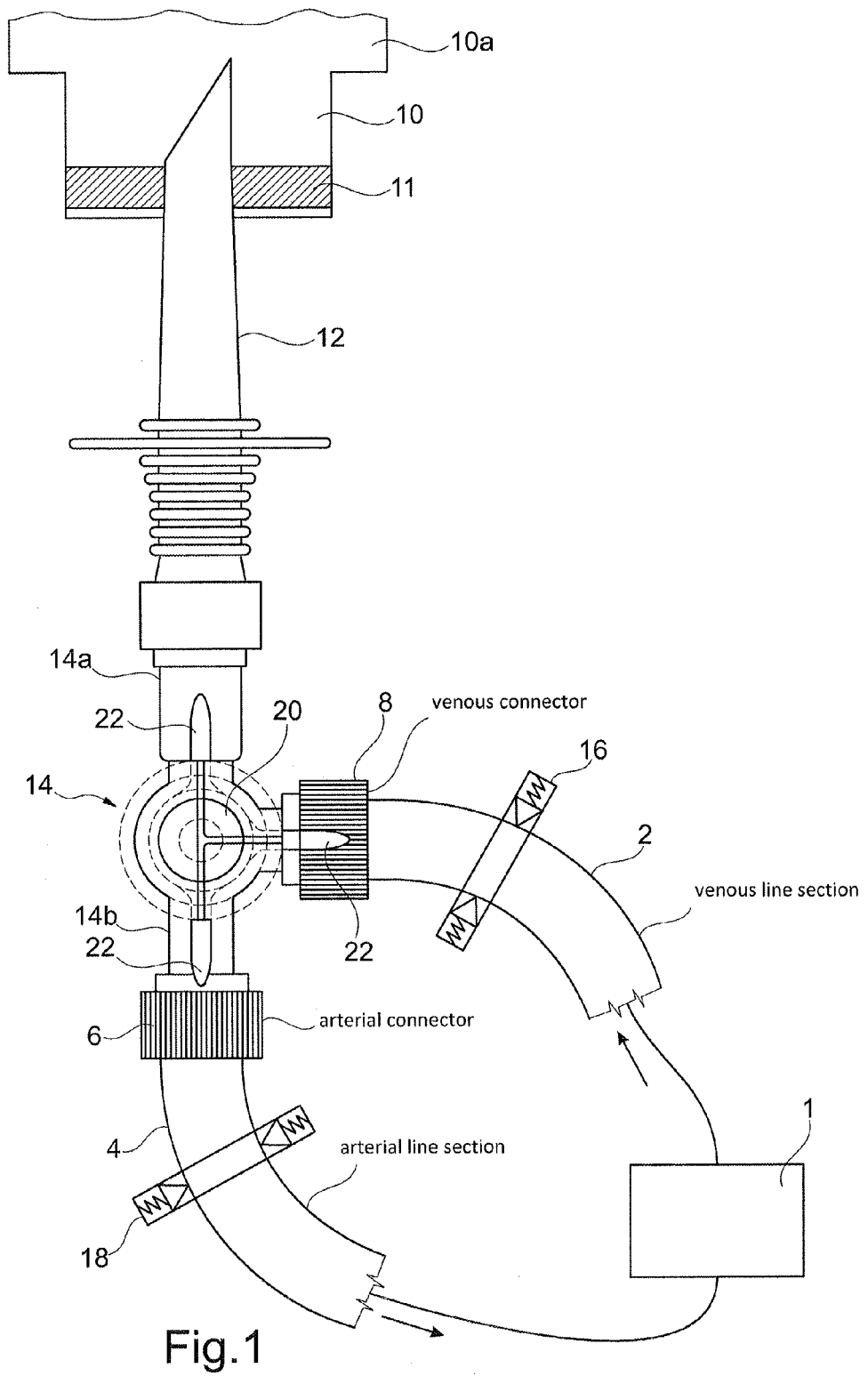
FIG. 1 shows a fluid system, preferably in the form of a circulation device, of an extracorporeal blood treatment device according to a preferred exemplary embodiment of the invention.

According to FIG. 1, the filling/circulation device according to aspects of the invention in hand has a fluid source, preferably in the form of a universal fluid container (NaCl bottle) 10, with a single outlet 11 which is punctured in the exemplary embodiment in hand with a spike 12 of the filling device in order to tap fluid from the fluid container 10. The design of spike 12 matches known spike structures so that its design does not have to be explained in more detail here. Furthermore, it is to be pointed out that, for example, in case of a Luer-Lock or another fitting on the container side, the spike may be replaced by a suitable connecting piece on the side of the filling/circulation device.

Furthermore the filling/circulation device according to aspects of the invention has a fluid blocking mechanism in the shape of a 3-way switch, preferably a 3-way valve 14, which is arranged directly downstream of the spike 12 (connecting piece) in the direction of flow away from the fluid container 10. In the case in hand, the spike 12 is directly (without interposition of an additional line section) connected to the 3-way valve 14. As an alternative, the spike 12 can also be realised in one piece or as a modular unit with the 3-way valve 14.

For that purpose, the 3-way valve 14 has a first connector or fluid inlet 14a that is fluidically connected with the spike 12 and/or to which the the fluid source 10 can be/is connected. Furthermore, the 3-way valve 14 has a second connector 14b, to which the arterial line section 4 of the patient-side fluid conducting system of the extracorporeal blood treatment device 1 can be connected. Finally, the 3-way valve 14 has a third connector 14c, to which the venous line section 2 of the patient-side fluid conducting system of the extracorporeal blood treatment device 1 can be connected. The venous line section as well as the arterial line section 2, 4 are each equipped with a hose clamp 16, 18 or a similar blocking device in order to close the respective hose section temporarily as an option.

The 3-way valve 14 in hand has a manually operable rotary lock consisting of a rotating cylindrical valve piston 20 that is equipped/designed on the front side with a handle, preferably in the shape of (three) intervention vanes 22. The valve piston has a central longitudinal bore, of which three radial bores branch off at equal distances in circumferential direction. The intervention vanes 22 are arranged in such a way that they are aligned along the radial bores and so indicate the flow direction of the radial bores. Such a 3-way valve is sufficiently known from the state of the art so that a further description, in particular of its function, can be dispensed with here.

FIGS. 2 to 5 show the switch positions intended according to aspects of the invention of the 3-way valve 14 in dependence on the current operating phases of the extracorporeal blood treatment device 1, which are described below in connection with the functions intended to be performed with it.

Figure 2:
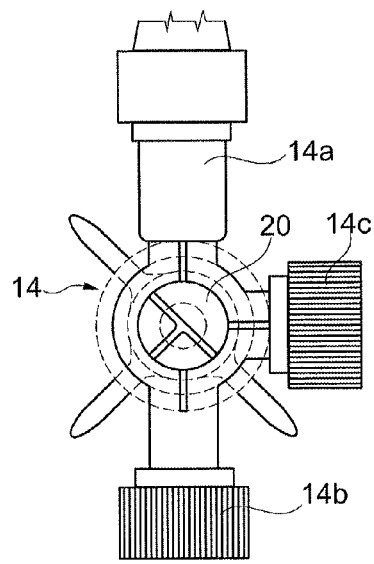
FIG. 2 shows a "closed switch position" of a filling device in the form of a 3-way valve of the circulation device according to FIG. 1 as a possible variant of the filling device according to aspects of the invention (here 3-way switch), whereby it is already pointed out here that, for example, a Y- or T-piece with hose blocking mechanism (hose clamps) can also be provided on each branch conduit upstream of the internal filling device connectors.

According to FIG. 2, the 3-way valve 14 is shown in a shut-off position in which all three connectors 14a-14c are closed. In this switch position, spike 12 can puncture the outlet 12 of the universal fluid reservoir 10 and so tap the fluid stored in there (in the chamber 10a formed by the container) without losing fluid into the atmosphere.

Figure 3:
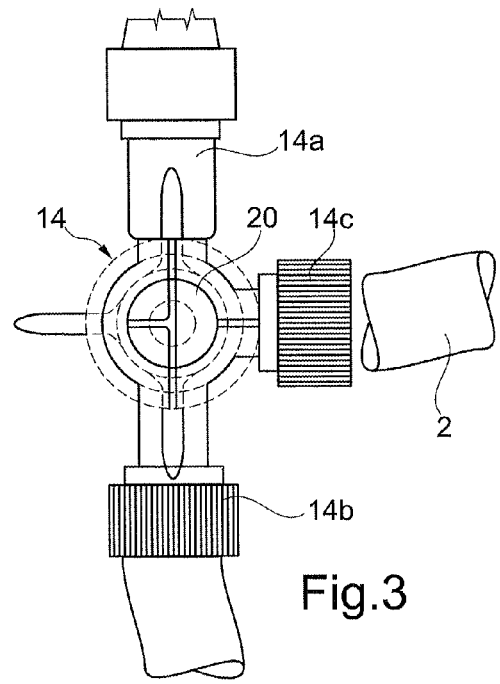
FIG. 3 shows a "flush position" of the 3-way valve of the circulation device according to FIG. 1, in which a fluid source (fluid container) is exclusively fluidically connected with an arterial line section of the extracorporeal blood treatment device.

FIG. 3 shows the so-called "flush position" in which the first connector 14a is fluidically connected with the second connector 14b, while the third connector 14c is closed. In this switch position, the arterial line section 4 is already connected to the second connector 14b, but the venous line section 2 is open to the atmosphere or connected to a drain/receiver tank.

In this switch position, fluid (NaCl solution) is conducted from the conventional fluid container with a single connector through the 3-way valve 14 in the arterial line section 4 and thus the patient-side fluid conducting system is flooded constantly until the fluid runs out of the venous line section 2 or runs into a drain/receiver tank. This means that the venous line section 2 serves as air vent during this system filling process. It has to be pointed out that the hose clamps 16, 18 are naturally open during this process.

Figure 4:
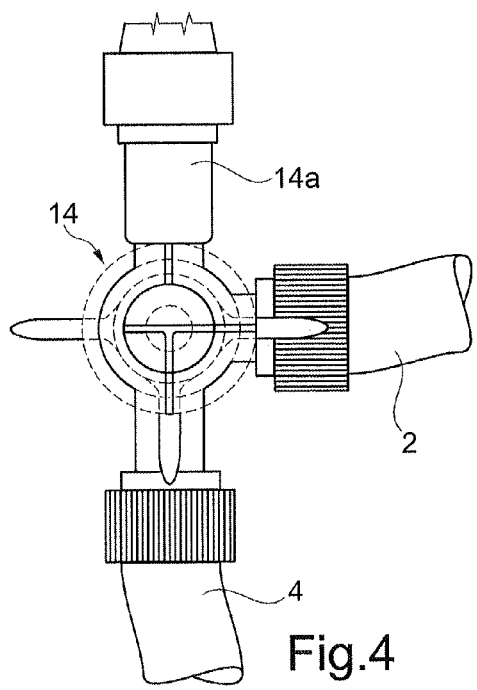
FIG. 4 shows a "circulation switch position" of the 3-way valve of the circulation device according to FIG. 1, in which the arterial line section is exclusively fluidically connected (short-circuited) with a venous line section of the extracorporeal blood treatment device and the fluid source is fluidically separated from the extracorporeal blood treatment device.
Figure 5:
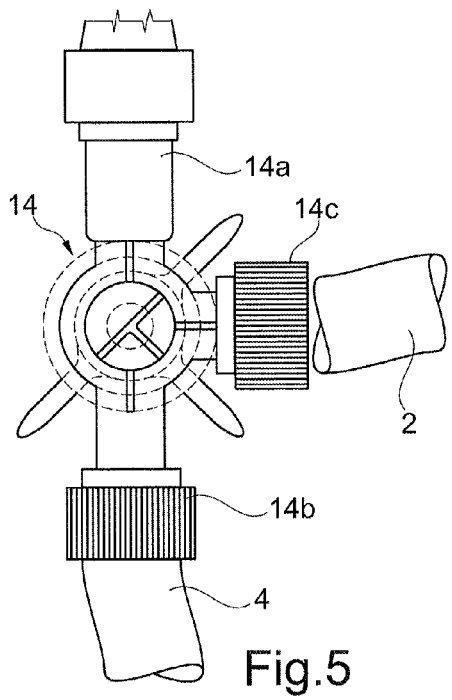
FIG. 5 shows another "closed switch position" of a 3-way valve of the circulation device according to FIG. 1.

As soon as the system has been filled with fluid from the fluid container 10, the venous line section is connected to the third connector 14c of the 3-way valve 14, and the 3-way valve 14 is put in the switch position according to FIG. 4, which can be referred to as "circulation" switch position. In this switch position, the second and third connectors 14b, 14c of the 3-way valve 14 are fluidically connected with each other, whereas the first connector 14a is closed.

If now the fluid contained in the fluid conducting system is circulated, it flows, starting from the venous line section 2, through the 3-way valve 14, and from there, is again passed on in the arterial line section 4 without fluid being able to enter the fluid container 10. Consequently, the fluid stored in there remains uncontaminated.

After a predetermined time of circulation, the 3-way valve 14 is switched further in the switch position shown in FIG. 5, in which again all three connectors 14a -14c are closed. You can see that the switch position according to FIG. 5 differs from the switch position according to FIG. 2 because the valve piston 20 was not simply turned back all the way in the first shut-off position according to FIG. 2, but was turned back in the second shut-off position according to FIG. 5, which is consequently diametrically opposite the first shut-off position. If the valve piston 20 had been turned back all the way, it would at least temporarily have passed through the "flush position", in which contaminated fluid from the fluid conducting system could possibly have penetrated the fluid container.

As soon as the 3-way valve 14 is closed, the venous line section 2 is now again disconnected from the 3-way valve 14 and the valve piston 20 is turned in the flush position according to FIG. 3 in order to perform a repeated flushing after circulation. Upon completion of this process, the filling/circulation cycle is completed.

Finally, the 3-way valve 14 is closed again, all hose clamps 16, 18 downstream of the 3-way valve 14 are put in the shut-off position, and the arterial line section is also disconnected from the 3-way valve 14 so that it can be connected together with the venous line section to the patient's body.

Here it has to be pointed out that according to the description in hand, the filling device according to aspects of the invention is designed with the 3-way switch as a fluid blocking mechanism so that a circulation mode can be performed. However, it is also conceivable to design the blocking mechanism according to aspects of the invention as a simple closing valve with an inlet connector and an outlet connector, which then allows only a "flushing mode" according to the definition above. In every case, the filling device according to aspects of the invention in hand allows a preferably manual closing of the spike outlet so that the spike can remain in the fluid container upon completion of the "flushing mode" and at least the arterial line section disconnected from it can be connected up with its internal connector to the patient access that was already established without further measures having to be taken.

Furthermore, it is conceivable to provide another (or alternatively to the fully closed switch position) switch position for the 3-way switch in which all three conduits are open and thus fluidically connected with each other. This position is technically relevant if sterile products are used, for example.

FIGS. 6a, 6b, 6c, and 6d show the filling device of the figures above, in particular in the area of the anti-contamination device 100 according to aspects of the invention.

Accordingly, between the spike 12 and the one connector (inlet) 14a of the 3-way valve 14, a non-return valve 110 is provided, which allows a fluid flow from the spike 12 in the direction of the 3-way valve 14 and blocks a fluid flow in the opposite direction. The non-return valve 110 has a valve body 112, which is pre-tensioned with a spring 116 against a valve seat 114 in order to close it against the fluid flow coming from the spike 12.

FIGS. 6a, 6b, 6c, and 6d show different variants for the positioning of the non-return valve 110.

According to FIG. 6a, the non-return valve 110 is coupled directly with the spike 12, and that without interposition of a connecting hose. For example, the non-return valve 110 could, in this case, be directly connected to the outlet connector of the spike 12 or even integrated in it. Furthermore, between the non-return valve 110 and the 3-way valve 14, preferably a connecting hose element 120 of a predetermined length could be arranged, whereby the length is selected in such a way that a hose volume is created that suffices to absorb a certain quantity of back-flowing fluid before it reaches the non-return valve 110 and/or the spike. This means that the connecting hose element 120 constitutes a kind of buffer storage that contributes to improved anti-contamination, in particular if the non-return valve 110 is defective and does not close all the way.

According to FIG. 6b, in the connecting hose element 120 between the spike 12 and the 3-way valve 14, a drip chamber 130 is interposed, which is equipped with a non-return valve function. Here the drip chamber 130 can also be mounted directly on the spike 12, whereby the downstream connecting hose element 120 constitutes the buffer storage described above.

Figure 6C:
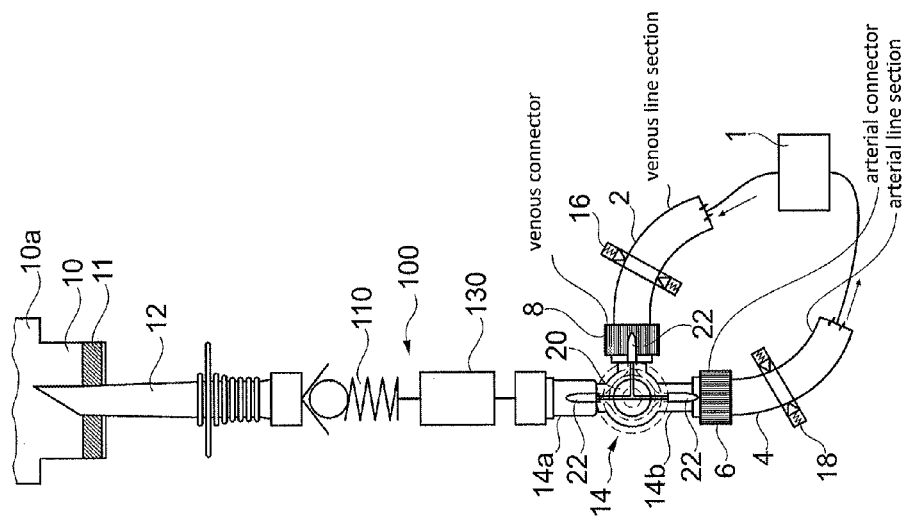
Figure 6D:
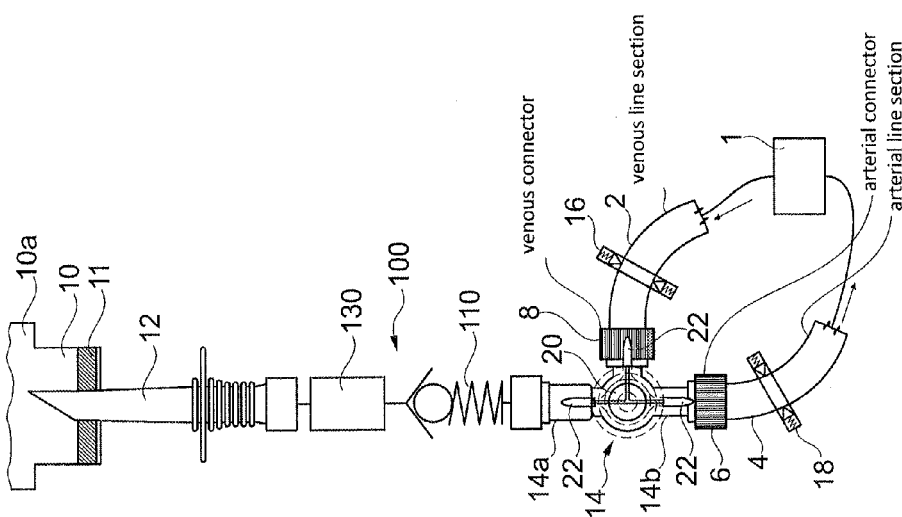

As an alternative to that, however, it is also possible to combine the non-return valve 110 according to FIG. 6a with a drip chamber 130 by arranging the non-return valve according to FIG. 6c downstream of the drip chamber 130 or according to FIG. 6d upstream of the drip chamber 130.

Finally it is to be pointed out that in particular the non-return valve 110 is an additional component, as compared to known devices, which could be damaged or yanked off by external impact. In order to avoid this, it is possible to connect the non-return valve 110 directly on the spike 12 and/or on the 3-way valve 14 or to integrate it in their connectors in order to create a modular unit in that way.

In summary, the invention in hand concerns a filling device, for example in the form of a circulation device of an extracorporeal blood treatment device 1, with a preferably universal medical fluid container 10, to which an arterial line section 4 of a fluid conducting system of the extracorporeal blood treatment device 1 can be connected as an option. Furthermore, the filling device has an anti-contamination device with a spike as well as a manual fluid blocking mechanism, for example a 3-way switch, preferably a 3-way valve, which is arranged (directly) downstream of the spike 12. A conduit 14a of the 3-way switch is coupled with the spike 12 or a similar connecting device or is formed in one piece together with it. Between the spike 12 and the manual fluid blocking mechanism 14, a non-return valve 110 is interposed, which is aligned in such a way that it automatically blocks a fluid flow in the direction of the fluid container 10.

The invention claimed is:

1. Filling device of a fluid conducting system of an extracorporeal blood treatment device comprising:
    an anti-contamination device with a spike;
    a manually operable fluid blocking mechanism including at least one fluid outlet connector adapted for detachable connection with an arterial blood line section of the fluid conducting system while the filling device is in operation, wherein the fluid blocking mechanism is a 3-way valve having a first conduit, a second conduit, and a third conduit, and is arranged downstream of the spike;
    a non-return valve positioned between the spike and the fluid blocking mechanism, the non-return valve adapted to only allow a flow from the spike in the direction of the fluid blocking mechanism;
    a fluid or liquid container connected via the spike is coupled with the arterial blood line section of the fluid conducting system for the filling process for a filling process based on a single-pass principle by configuring the 3-way valve in a first switch position in which the first conduit is fluidically connected with the second conduit to which the arterial blood line section is coupled and the third conduit is closed;
    wherein in a second switch position of the 3-way valve, the arterial blood line section is connected with a venous line section for a circulation process, whereby in this second switch position, the first conduit of the 3-way valve is closed so the fluid or liquid container is fluidically separated from the fluid conducting system of the extracorporeal blood treatment device and the second conduit is fluidically connected with the third conduit connected to the venous line section; and
    wherein in a third switch position of the 3-way valve, all conduits of the 3-way valve are closed such that the arterial blood line and the venous line sections of the fluid conducting system are disconnected from the fluid container.

2. Filling device according to claim 1, wherein the non-return valve has a valve body that can be activated by the fluid from the fluid container, the valve body pre-tensioned on a valve seat by a spring against the direction of flow from the spike.

3. Filling device according to claim 1, wherein the spike and the non-return valve are combined in a unit by integrating the non-return valve in a connector of the spike.

4. Filling device according to claim 1, wherein the fluid blocking mechanism and the non-return valve are combined in a unit by integrating the non-return valve in an inlet connector of the fluid blocking mechanism on which the spike is connected.

5. Filling device according to claim 1, wherein the spike, the fluid blocking mechanism, and the non-return valve are integrated in a unit in which the spike is coupled directly at a coupling point with the fluid blocking mechanism and the non-return valve arranged at the coupling point.

6. Filling device according to claim 1, further comprising a drip chamber element arranged downstream of the spike and the non-return valve, the drip chamber element connected with the fluid blocking mechanism through a connecting hose or pipe of a predetermined length.

7. Filling device according to claim 1, wherein the fluid blocking mechanism is a manually operable closing valve.

8. Filling device according to claim 1, wherein the 3-way valve includes a rotary piston with a handle.

9. Filling device according to claim 1, wherein the spike is connected as a connecting device with a Luer-Lock fitting to the fluid blocking mechanism or is combined with the fluid blocking mechanism into an integral modular unit.

10. Filling device according to claim 1, wherein the spike is connected transition-free without interposition of a bridging line section directly with the fluid blocking mechanism.

11. Medical fluid conducting system of a blood purification device with an arterial blood line section and a venous line section, on the line ends of which one connector each is provided, further comprising a filling device according to claim 1, to which at least the arterial blood line section can be connected.

12. Medical fluid conducting system according to claim 11, wherein at least the arterial blood line section has, directly downstream, a blocking mechanism that temporarily fluidically disconnects and reconnects the arterial blood line section from the filling device.

13. Medical fluid conducting system according to claim 11, wherein the venous line section has, directly downstream, a blocking mechanism, that temporarily fluidically disconnects and reconnects the venous line section from the filling device.

14. Procedure for performing a filling and recirculating process of a blood-side conducting system of a dialysis machine using a filling device according to claim 1, the procedure comprising:
    connecting the spike to a single fluid connector of the fluid container with the 3-way valve completely closed, and connecting the arterial blood line section to the second conduit of the still closed 3-way valve with the venous line section open to the environment;
    flushing a fluid flow path along the arterial blood line section of the extracorporeal blood treatment device and the venous line section by fluidically connecting the spike with the second conduit of the 3-way valve;
    complete closing of the 3-way valve and connecting the venous line section to the third conduit of the 3-way valve;
    recirculating filled-in fluid in the fluid flow path by short-circuiting the second and third conduits on the 3-way valve while simultaneously closing flow from the spike;
    complete closing the 3-way valve and uncoupling the venous fluid line section from the third conduit and repeating the flushing of the fluid flow path step; and
    complete closing of the 3-way valve in preparation for a subsequent connecting of the filled arterial blood and venous line sections to a patient.

15. Use of a filling device according to claim 1 to fill a blood-side fluid conducting system of a dialysis machine.

* * * * *